United States Patent [19]

Lemole

[11] Patent Number: 4,512,346
[45] Date of Patent: Apr. 23, 1985

[54] STERNAL CLOSURE METHOD AND MEANS

[76] Inventor: Gerald M. Lemole, 404 Tomlinson Rd., Huntingdon Valley, Pa. 19046

[21] Appl. No.: 488,280

[22] Filed: Apr. 25, 1983

[51] Int. Cl.³ ............... A61B 17/08; A61B 17/04; A61F 5/04
[52] U.S. Cl. ............... 128/335; 128/92 B; 128/92 D; 128/334 C
[58] Field of Search ............... 128/92 R, 92 B, 92 D, 128/92 G, 335, 334 R, 334 C

[56] References Cited

U.S. PATENT DOCUMENTS

| 887,074 | 5/1908 | Depage | 128/92 B |
| 4,078,559 | 3/1978 | Nissinen | 128/92 R |
| 4,146,022 | 3/1979 | Johnson et al. | 128/92 B |
| 4,201,215 | 5/1980 | Grossett et al. | 128/335 |
| 4,210,148 | 7/1980 | Stivala | 128/335 |
| 4,269,180 | 5/1981 | Dall et al. | 128/92 B |

FOREIGN PATENT DOCUMENTS

| 2911748 | 10/1980 | Fed. Rep. of Germany | 128/92 B |
| 2438464 | 5/1980 | France | 128/335 |

OTHER PUBLICATIONS

Sluss, *Emergency Surgery*, 1931, p. 581, Blakiston's & Son & Co., Phila., PA.
Bickham, *Operative Surgery*, vol. 1, 1924, pp. 266-269, (FIG. 243, p. 267).

Primary Examiner—C. Fred Rosenbaum
Assistant Examiner—C. W. Shedd
Attorney, Agent, or Firm—Robert J. Mooney

[57] ABSTRACT

An improved sternal closure device and method for using the device is disclosed wherein a pair of thin rods of appropriate length are positioned longitudinally along respective opposite sides of a severed sternum on the posterior surface thereof. Individual wires secured at one end thereof to corresponding points along each rod are passed through matching holes on either side of the severed sternum to extend beyond its anterior surface. Opposing pairs of wires transversely oriented are tensioned to draw the sternum together and knotted thereby holding the sternum closed with forces applied by the wires and distributed along the length of the sternum via the rods. Alternatively, the wires may have looped inner ends that engage the rods on the posterior surface of the sternum for distribution of the closing forces.

5 Claims, 6 Drawing Figures

STERNAL CLOSURE METHOD AND MEANS

BACKGROUND OF THE INVENTION

The present invention relates to surgical devices and techniques, and more particularly to an improved means and method for closing a severed sternum following major chest surgery.

During the course of a major thoracic surgical procedure, particularly that of open heart surgery, the sternum is split longitudinally to allow sufficient access to the organs within the thoracic cavity. Upon completion of the surgical procedure, the sternum must be rejoined and closed securely to insure proper healing. Such sternal closure has heretofore typically involved the use of several suture wires each individually looped through matching holes on either side of the severed sternum. The wire loops, each brought transversely together in front of the sternum, are hand tensioned to rejoin the sternum, twisted together to secure its closure and snipped above the twist.

Aside from the inherent disadvantage of substantially prolonging an already complex and traumatic surgical procedure by the handling of separate suture wires, the sternum closing technique described above can lead to numerous adverse consequences due primarily to the tensioned, transversely oriented wire loops cutting through the sternum. Such cutting of the sternum can cause bleeding and result in macerative damage to the cartilage and associated muscle tissue with a consequent increase in postoperative discomfort and in the time required for healing.

SUMMARY OF THE INVENTION

Accordingly, it is a general purpose and object of the present invention to provide an improved means and method for closing a sternum severed during major chest surgery.

A more particular object of the present invention is to provide a sternal closure device that firmly joins a severed sternum during major chest surgery while reducing the risk of postoperative damage to the sternum and the complications caused thereby.

A further object of the present invention is to provide an effective sternal closure method that facilitates closing of a severed sternum during major chest surgery to minimize the overall time of the surgical procedure.

A still further object of the present invention is to provide a means and method for sternal closure that is simple yet reliable, safe to manipulate, and easily adapted to existing surgical procedures.

Briefly, these and other objects of the present invention are accomplished by an improved sternal closure device and method for using the device wherein a pair of thin rods of appropriate length are positioned longitudinally along respective opposite sides of a severed sternum on the posterior surface thereof. Individual wires secured at one end thereof to corresponding points along each rod are passed through matching holes on either side of the severed sternum to extend beyond its anterior surface. Opposing pairs of wires transversely oriented are tensioned to draw the sternum together and twisted together thereby holding the sternum closed with forces applied by the wires and distributed along the length of the sternum via the rods. Alternatively, the wires may have looped inner ends that engage the rods on the posterior surface of the sternum for distribution of the closing forces.

For a better understanding of these and other aspects of the present invention, reference may be made to the following detailed description taken in conjunction with the accompanying drawing in which like reference numerals designate like parts throughout the figures thereof.

DESCRIPTION OF THE PREFERRED EMBODIMENT

Figure 1:
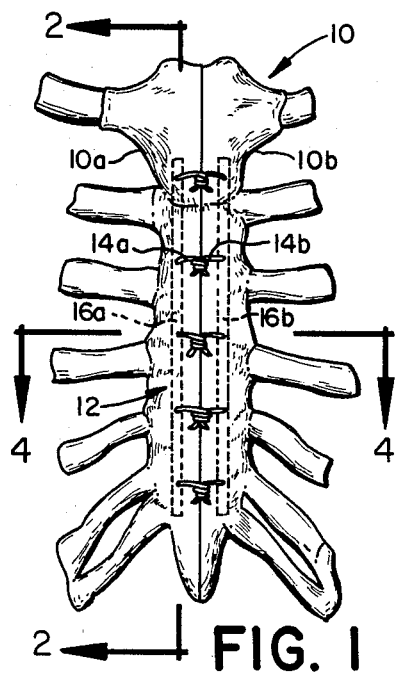
FIG. 1 is a frontal view of a severed sternum closed in accordance with the present invention.

Referring now to FIG. 1, there is shown the anterior surface of the body of a severed sternum 10 rejoined by means of a sternal closure device, generally designated as 12. Typically, the sternum 10 is split logitudinally into two pieces 10a and 10b during the performance of major chest surgery, such as that of open heart surgery, with firm and secure closure being required thereafter to permit proper postoperative recovery.

In accordance with the present invention, the sternal closure device 12 includes a series of opposing wire elements 14a and 14b each secured at one end thereof, as described in greater detail hereinafter, along the length of a respective one of a pair of rods 16a and 16b located on either side of the sternum 10 along its posterior surface. The rods and the wire elements are made from a strong, durable, non-reactive and noncorrosive metallic material, such as stainless steel. The wire elements 14a and 14b are of typically narrow gauge and are formed in lengths sufficient to permit extended passage from the posterior to anterior surface of the sternum 10, as better seen in FIG. 2. Along the anterior surface of the severed sternum 10, the opposing wire elements 14a and 14b are twisted together, after being appropriately tensioned, so that the separate pieces 10a and 10b of sternum 10 are held closed with forces applied by the twisted wires but distributed along the length of the sternum through the rods 16a and 16b.

Figure 2:
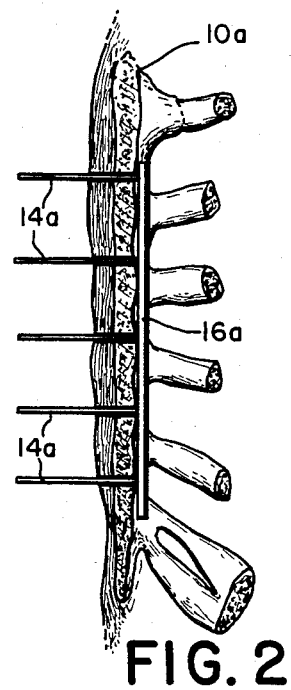
FIG. 2 is a longitudinal sectional view of the sternum shown in FIG. 1 taken generally along the line 2—2.

Referring now to FIG. 2 in conjunction with FIG. 1, the rods 16a and 16b are positioned longitudinally along respective separate pieces 10a and 10b of severed sternum 10 on the posterior surface thereof. The rods 16a and 16b are disposed along the posterior surface of the severed sternum 10 so that the respective wire elements 14a and 14b are oriented substantially normal to the surface and may be passed through matching holes conventionally formed in the respective sternum pieces 10a and 10b. Fabricated of a metallic material similar to that of wire elements 14a and 14b, the rods 16a and 16b are formed having a relatively small diameter to facilitate placement on the posterior surface of the sternum and are formed with a length sufficient to extend substantially the length of the body of sternum 10, typically between 10 or 15 centimeters.

Figure 3A:
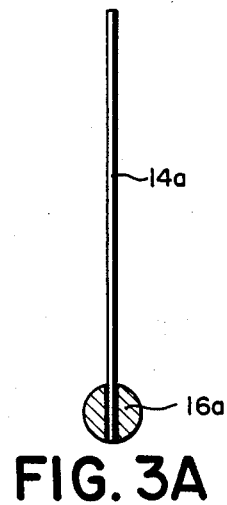
FIG. 3A is an enlarged partial cross-section of one construction of the sternal closure device of the present invention.
Figure 3B:
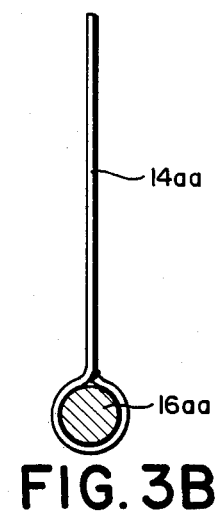
FIG. 3B is an enlarged partial cross-section of another construction of the sternal closure device of the present invention.

Referring now to FIG. 3A in conjunction with FIG. 2, each wire element 14a and 14b is secured at one of its ends to respective rod 16a and 16b at points along the length thereof. Spaced apart and substantially aligned along the respective rods 16a and 16b, the wire elements 14a and 14b are preferably attached by inserting the end of each wire element diametrically through the respective rods and uniting the similar metallic materials thereof using conventional metal fusing techniques. As an alternative means of attachment to a respective rod 16aa, wire elements 14aa may be formed to have looped inner ends for engaging about the periphery of respective rods 16a and 16b at selected points along their lengths as shown in FIG. 3B. In either case, the closing force exerted by the wires is distributed along the length of the sternum 10 via the rods.

Figures 4A, 4B:
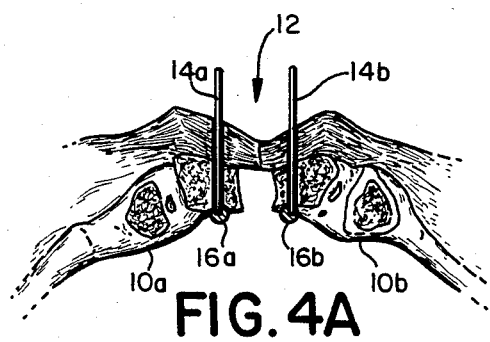
FIG. 4A is a transverse sectional view of the sternum of FIG. 1 taken generally along the line 4—4 prior to closure in accordance with the present invention.
FIG. 4B is a transverse sectional view of the closed sternum shown in FIG. 1 taken generally along the line 4—4.

The method of using the sternal closure device 12 of the present invention can be described with reference to FIGS. 4A and B. With the severed sternum 10 spread open following a major chest operation, rods 16a and 16b, having the respective series of wire elements 14a and 14b secured thereto, are inserted against the posterior surface of each of the separate pieces 10a and 10b of the sternum. Inserted through matching holes, typically formed with heat, in the cartilage of the separate sternum pieces 10a and 10b, the series of wire elements 14a and 14b are pulled outward to project substantially beyond the anterior surface of sternum 10. In the event that wire elements 14aa having looped inner ends are employed, the rods 16a and 16b are passed through the respective looped ends after insertion of the wires on both sides of severed sternum 10 and before the wires are pulled outward to place the rods in proper position along the posterior of the sternum pieces 10a, and 10b.

After extending the wire elements 14a and 14b outwardly and positioning the rods 16a and 16b immediately adjacent to the posterior surface of the respective sternum pieces 10a and 10b, the outer ends of opposing pairs of the wire elements are tensioned and knotted together by twisting while the severed sternum 10 is drawn closed. As viewed in FIG. 4B, the rods 16a and 16b anchor the transversely oriented, knotted wire elements 14a and 14b and thereby serve to distribute the closing forces of the wire elements along the length of the sternum 10 rather than isolating those forces at the separate transverse locations of the wires.

Therefore, it is apparent that the disclosed invention provides an improved means and method for closing a sternum severed during major chest surgery, particularly providing a sternal closure device that effectively draws together and firmly joins the sternum with a reduction in the risk of postoperative damage thereto. Furthermore, the present invention provides an effective sternal closure method that faciliates closing the sternum during major chest surgery to minimize the overall time of the surgical procedure. In addition, the disclosed sternal closure device is simple yet reliable, safe to manipulate, and easily adapted to existing surgical procedures.

Obviously, other embodiments and modifications of the present invention will readily come to those of ordinary skill in the art having the benefit of the teachings presented in the foregoing description and drawings. It is therefore to be understood that various changes in the details, materials, steps and arrangement of parts, which have been described and illustrated to explain the nature of the invention, may be made by those skilled in the art within the principle and scope of the invention as expressed in the appended claims.

I claim:

1. A device for closing a severed sternum, comprising:
   a pair of rods each to be disposed longitudinally along respective separate sides of the sternum immediately adjacent to the posterior surface thereof; and
   a plurality of wires each connected at one end thereof to corresponding points along each of said rods, said wires to be extended through the respective separate sides of the sternum and be connected at their other ends in opposing pairs on the anterior surface of the sternum.

2. A sternal closure device according to claim 1, wherein:
   said wires are connected to respective ones of said rods by fusing.

3. A sternal closure device according to claim 1, wherein:
   said wires are provided with a looped inner end for engaging about respective ones of said rods.

4. A method for closing a severed sternum with a pair of rods and a plurality of wires each connected at one end thereof to corresponding points along each rod, comprising the steps of:
   providing a matching series of holes through opposite sides of the severed sternum;
   inserting the wires through the holes from the posterior surface of the sternum until the rods are disposed along the opposite sides of the sternum immediately adjacent to the posterior surface thereof;
   tensioning the wires to draw the severed sternum together; and twisted together opposing pairs of the wires on the anterior surface of the sternum.

5. A method for closing a severed sternum with a pair of rods and a plurality of wires each terminated at one end thereof with a closed loop, comprising the steps of:
   providing a matching series of holes through opposite sides of the severed sternum;
   passing each wire through a respective one of the holes from the posterior surface of the sternum;
   inserting the rods through the looped ends of the wires on respective opposite sides of the sternum adjacent to the posterior surface thereof;
   tensioning the wires to draw the severed sternum together; and twisted together opposing pairs of the wires on the anterior surface of the sternum.

* * * * *